US00PP08264P

United States Patent [19]

Dehan

[11] Patent Number: Plant 8,264

[45] Date of Patent: Jun. 15, 1993

[54] IMPATIENS PLANT NAMED DANSERRA

[75] Inventor: Klara Dehan, Holon, Israel

[73] Assignee: Danziger- "Dan" Flower Farm, Moshav Mishmar Hashiva, Israel

[21] Appl. No.: 755,519

[22] Filed: Aug. 29, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A distinct Impatiens cultivar named Danserra, characterized by its medium size, red-purple flowers, large dark green foliage, and its compact growth habit.

1 Drawing Sheet

1

The present inventiton relates to a new and distinctive cultivar of Impatiens plant, botanically known as Impatiens, and known by the cultivar name Danserra. Danserra was developed by me through controlled breeding by crossing a cultivar identified by breeding number F-42 as the seed parent with the cultivar identified as 187-15-A as the pollen parent. Both parents are unreleased, proprietary lines.

Asexual reproduction by cuttings at Mishmar Hashiva, Israel, has shown that the unique features of this new impatiens are stabilized and are reproduced true to type in successive propagations. The cuttings preferably comprise tip cuttings with at least one auxiliary bud, which is vegetative and not a flower bud.

The following characteristics distinguish the new Impatiens from both its parent varieties and other cultivated Impatiens of this type known and used in the floriculture industry:

1. Medium size, red-purple flowers.
2. Large dark green foliage.
3. Compact growth habit.

The accompanying color photographs illustrate the overall appearance of this cultivar, showing the colors as true as it is reasonably possible to obtain in a colored reproduction of this type.

The top photograph is a top perspective view showing the flowers and foliage of a portion of a plant of Danserra.

The bottom photograph is an enlarged closeup of a single flower and surrounding foliage.

The following is a detailed description of my new Impatiens cultivar based on plants produced under commercial practice during the spring in Mishmar Hashiva, Israel.

Color references are made to The Royal Horticultural Society Colour Chart except where general terms of ordinary dictionary significance are used.

Parentage:

*Male parent.*—187-15-A.

*Female parent.*—F-42.

Propagation:

A. *Type cutting.*—Tip cuttings with at least one axillary, vegetative bud.

B. *Time to initiate roots.*—8–10 days both at 25°–30° C. summer, and 20°–22° C. winter.

C. *Rooting habit.*—Good root initiation.

Plant description:

A. *Form.*—Compact, mounded, symmetrical.

B. *Habit of growth.*—Compact growth habit.

2

C. *Foliage description.*—(1) Size: Large, approximately 13 cm long and 4.5 cm wide. (2) Shape: Oval, with acuminate tip. (3) Margin: Finely serrated. (4) Color: Young foliage top side 137A; under side 147B. Mature foliage top side 147A; under side 147B. (5) Venation: Green, tinged with purple.

Flowering description:

A. *Flowering habits.*—From bud to open flower requires approximately five (5) days.

B. *Natural flowering season.*—Spring and the summer in moderate climates. In Israel flowering also occurs in the winter.

*Flower buds.*—Normal. Spurs up to 5.0 cm long on mature buds with throat originating from major sepal; the wide, oval part of the spur is 0.9 cm by 1.0 cm and close to 60C-D in color; the long part is approximately 4.0 cm in length, almost straight, and close to 60C-D in color.

D. *Flowers borne.*—Flower buds are presented at the tips of stems overlying the terminal whorls of leaves. At most stems, there are generally about 5–6 buds in different stages of maturity, and normally about 2–3 or more open blooms, as the plant reaches market stage. Two or more flower buds are often borne at each leaf axis.

E. *Quantity of flowers.*—Floriferous; total inflorescence is approximately 30 flowers three months after planting. Flowering is continuous at temperatures above approximately 10° C. and with at least minimum levels of light.

F. *Petals.*—(1) Shape: Two pairs of heart shaped petals, each petal of each pair measuring approximately 2.2 cm from base to tip and 2.0 cm at its broadest point; single petal is relatively larger and oval shape, measuring approximately 3.0 cm along its major axis. (2) Color: Top side in spring when opening 67A, with little or no fading; underside also 67A. (3) Number of petals: Five. (4) Size of flowers: Approximately 4.5 cm in diameter.

G. *Reproductive organs.*—(1) Stamens: One in number. (a) Anther color: Green. (b) Pollen color: White. (2) Pistils: (a) Stigma: Cone shaped; green in color. (b) Style: Light Green in color. (c) Ovaries: One in number; size 1.5 mm; color light green.

Disease resistance: Unknown.

I claim:

1. A new and distinct cultivar of Impatiens plant named Danserra, as illustrated and described.

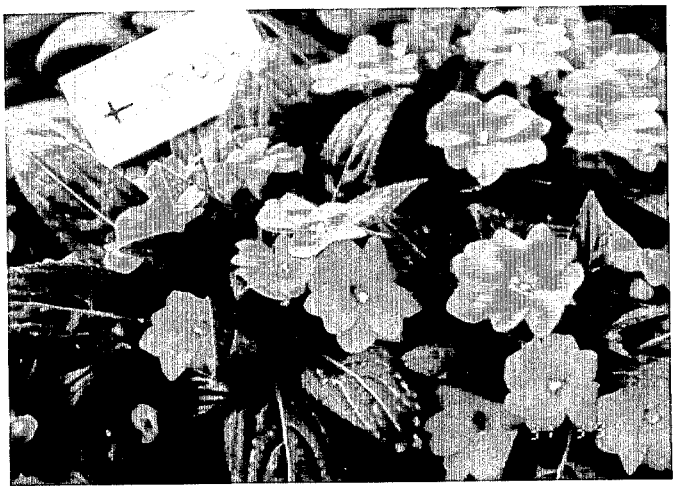
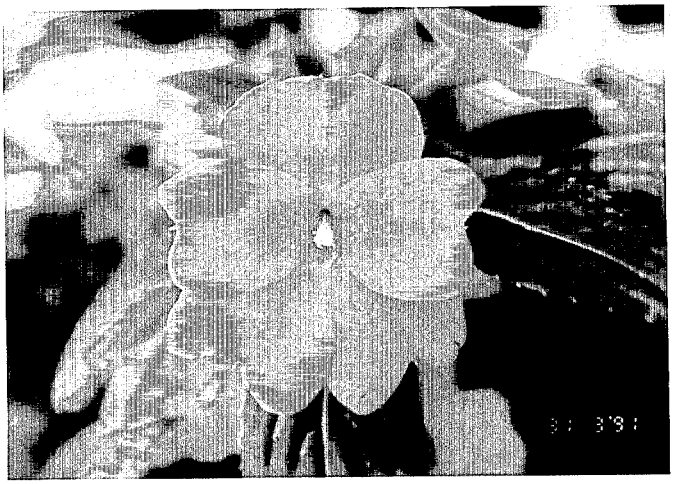

* * * * *